United States Patent [19]

Ishimaru et al.

[11] 4,091,217
[45] May 23, 1978

[54] 7-((5'-N-METHYLTHIOACETAMIDO)-ADIPOAMIDO)CEPHALOSPORIN DERIVATIVES

[76] Inventors: Toshiyasu Ishimaru, D-14, 2-7, Momoyamadai, Suita; Mariko Kawabata, 9-4, Tachibanacho-1 chome, Toyonaka, both of Japan

[21] Appl. No.: 748,756

[22] Filed: Dec. 9, 1976

Related U.S. Application Data

[62] Division of Ser. No. 580,965, May 27, 1975, Pat. No. 4,036,833.

[30] Foreign Application Priority Data

May 28, 1974 Japan ............................. 49-61296
Jul. 3, 1974 Japan ............................. 49-76771

[51] Int. Cl.² ............... C07D 501/22; C07D 501/28; C07D 501/40
[52] U.S. Cl. ..................................... 544/30; 544/17
[58] Field of Search ................. 260/243 C; 544/30

[56] References Cited

U.S. PATENT DOCUMENTS

| | | | |
|---|---|---|---|
| 3,865,819 | 2/1975 | De Marinis et al. | 260/243 C |
| 3,996,217 | 12/1976 | Breuer et al. | 260/243 C |
| 4,017,485 | 4/1977 | Hasegawa et al. | 260/243 C |
| 4,039,536 | 8/1977 | Takano et al. | 544/26 |

OTHER PUBLICATIONS

Flynn, Cephalosporins and Penicillins, (1973), pp. 13, 148 and 179.

*Primary Examiner*—Donald G. Daus
*Assistant Examiner*—David E. Wheeler
*Attorney, Agent, or Firm*—Hubbell, Cohen, Stiefel & Gross

[57] ABSTRACT

New N-substituted thio (or sulfinyl) aliphatic acylcephalosporin C and derivatives thereof in the 3-position have been prepared. The compounds are useful as intermediates for recovering cephalosporin C and deacetoxycephalosporin C from fermentation broths thereof and also for preparing 7-aminocephalosporanic acid and derivatives thereof in the 3-position.

9 Claims, No Drawings

7-((5'-N-METHYLTHIOACETAMIDO)-ADIPOAMIDO)CEPHALOSPORIN DERIVATIVES

This is a division of application Ser. No. 580,965, filed May 27, 1975, now U.S. Pat. No. 4,036,833.

This invention relates to new cephalosporin derivatives and a process for their preparation.

More particularly, the invention provides new cephalosporin derivatives of the general formula (I):

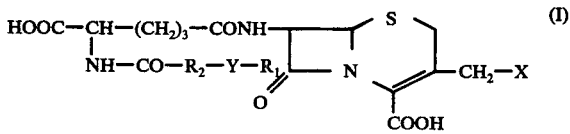

wherein $R_1$ is a lower alkyl group, an aryl group or an aralkyl group, $R_2$ is a lower alkylene group, Y is a sulfur atom or a sulfinyl group and X is a hydrogen atom, an acetoxy group, an azido group or a group of the formula —$SR_3$ in which $R_3$ is a heterocyclic group which may be substituted by methyl group(s), and salts or adducts thereof.

It is an object of the invention to provide new cephalosporin derivatives represented by the above formula (I) and salts or adduct thereof. Another object of the invention is to provide a process for the preparation of the compounds of formula (I). Still another object of the invention is to provide an industrially advantageous process for recovering cephalosporin C and deacetoxycephalosporin C from a fermentation broth thereof. Yet another object of the invention is to provide an industrially useful process for the preparation of 7-aminocephalosporanic acid and derivatives position, thereof in the 3-which compounds are key intermediates for various important cephalosporins. Further objects and features of the invention will become apparent in the following description.

There are known methods of recovering cephalosporin C; for example, U.S. Pat. No. 3,467,654 discloses that a fermentation broth of cephalosporin C is treated with acetone to precipitate impure materials which are filtered off, the filtrate is passed through an anion exchange resin to adsorb cephalosporin C on it and the cephalosporin C is then eluted with an acidic buffer. Japanese Patent Publication No. 61,494/1973 describes a method for extracting cephalosporin C which comprises acylating cephalosporin C with a halogeno aliphatic acid and adding quinoline to the mixture at about pH 3 to precipitate the quinoline salt of N-halogeno acyl-cephalosporin C. The latter method is a considerably improved one among the known methods for recovering cephalosporin C from a solution containing same, but it is still disadvantageous because the quinoline salt does not precipitate at a concentration of 1% or less of cephalosporin C and its recovery yield is also not good.

In view of these circumstances, and taking into consideration the fact that the cephalosporin C concentration in broths obtained by industrial fermentation is about 0.3%, the present inventors have achieved this invention as a result of various investigations on methods for recovering cephalosporin C in good yield and economically even from low concentration solutions thereof.

The invention provides a process for recovering cephalosporin C or its deacetoxy derivative which comprises reacting an aqueous solution containing cephalosporin C or its deacetoxy derivative with a reactive derivative of an acid of the general formula (II):

, wherein $R_1$, $R_2$ and Y are as defined above, to give an aqueous solution containing N-acyl-cephalosporin C or its deacetoxy derivatives of the general formula (III):

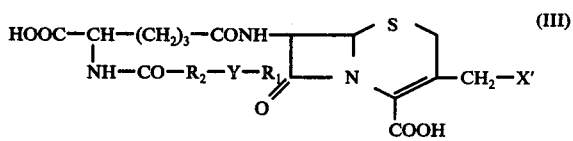

wherein X' is an acetoxy group or a hydrogen atom and $R_1$, $R_2$ and Y are as defined above, then adding quinoline is isoquinoline to the solution and adjusting it to about pH 2.0-3.5 by adding an acidifying agent and if needed, further adding an inorganic base thereto.

A low concentration aqueous solution containing 0.3 to 8% (W/V) cephalosporin C and/or its deacetoxy derivative may be used as the aqueous solution containing cephalosporin C or its deacetoxy derivative in the invention. Such aqueous solutions include fermentation broths of cephalosporin C or its deacetoxy derivative which are partially purified by conventional treatments known in the art, such as filtration, acetone treatment and ion-exchange resin treatment and the like, or are partially concentrated. However, it is not convenient to use a solution of too high a concentration of cephalosporin C, because of the difficulty of recovering an adducts of N-acylcephalosporin C with an organic base due to a tendency to become muddy. On the other hand, the use of very low concentration cephalosporin C solutions tends to lower its recovery yield. It also is not recommended, both technical and economical viewpoints, to concentrate the fermentation broth as mentioned above, because this requires a large heat source and laborious work and further results in undesirable decomposition of the cephalosporin C. In the invention it is therefor preferred to use a fermentation broth which has been subjected only to a partial purification to remove materials which might adversely influence the acylation, e.g., monoaminomonocarboxylic acid, or a fermentation broth which has been concentrated only slightly.

An aqueous solution containing cephalosporin C or its deacetoxy derivative of the above type is allowed to react with a reactive derivative of the acid of the formula (II).

The term "lower alkyl group" in the definition of $R_1$ includes straight or branched-chain alkyl group having one to five carbon atoms. Similarly, "lower alkylene group" in the definition $R_2$ includes straight or branched-chain alkyl groups having one to three carbon atoms.

Specific examples of the above acids are:

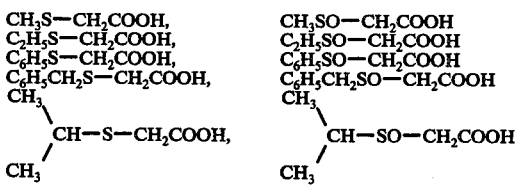

-continued

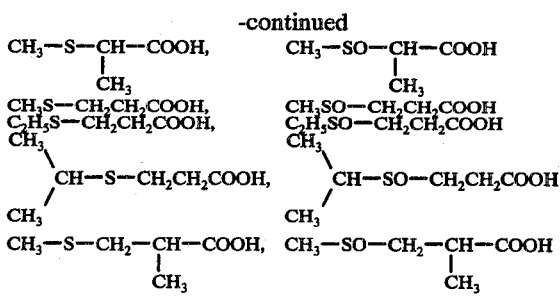

As the reactive derivatives of the above acids, it is desirable to use a reactive derivative which is capable of acylating the amino group in the side chain of cephalosporin C and its deacetoxy derivative at temperatures of about 0° to 30° C and at low concentration. It is also desirable to select the reactive derivative, taking economy into consideration. Thus, as preferred examples of the reactive derivatives to be used in the invention there may be mentioned the mixed anhydrides of the acid of the formula (II) with an aliphatic acid such as acetic acid, propionic acid, α-methylpropionic acid, butyric acid, α-ethylbutyric acid, valeric acid, pivaloic acid or 2-ethylhexanoic acid, or an alkyl halocarbonate such as ethyl chlorocarbonate, butyl chlorocarbonate or isobutyl chlorocarbonate. That is, preferred examples of other acids to be used as a raw material for the mixed anhydride are those having a dissociation constant of at least one-half and suitably about one-fifth of the dissociation constant of the acid of the formula (II). Moreover, acid halides or the like may be used.

The acylation may be preferably carried out at approximately 0°–30° C and pH 7–11, more preferably at about pH 8–9.5. It is preferred to maintain the desired pH during the acylation, adding an appropriate base or with addition of an appropriate buffer, because of the tendency of the pH value to drop.

The amount of the acylating agent to be used depends upon the kind of fermention broth to be treated. For example, in the case of a broth which has been subjected to a partial purification with an ion exchange resin, about 1.5 to 4.0 moles of the acylating agent per mole of cephalosporin C gives good results. In the case of a broth which has been subjected to a partial purification with acetone it is required to use about 4 to 7 moles of the acylating agent per mole of cephalosporin C.

The resulting N-acyl-cephalosporin C or its deacetoxy derivative of the formula (III) is treated with quinoline, isoquinoline or a mixture thereof to precipitate it from the aqueous solution. Moreover, it is not required that the base be very pure. The amount of the base to be used is about 2–5 moles per mole of N-acyl-cephalosporin C.

After addition of the base, the mixture is adjusted to pH 2.0–3.5 with an acidifying agent such as sulfuric acid, hydrochloric acid, nitric acid, phosphoric acid or the like and is stirred for about one hour at 0°–30° C, preferably 10°–20° C to precipitate N-acyl-cephalosporin C or its deacetoxy derivative with the base. This precipitate is considered to be an adduct and usually is crystalline in form.

Furthermore, when the resulting product is difficult to precipitate because of its concentration or other components in the reaction mixture, it is desirable to add to the reaction mixture an inorganic salt such as sodium sulfate or sodium chloride. Then the resulting precipitate may be separated by using conventional separation procedures, e.g., centrifugation or filtration, washed with water and then with an organic solvent such as ethyl acetate and then dried.

The thus obtained adduct of N-acyl-cephalosporin C or its deacetoxy derivative and the organic base may be converted into the corresponding other derivatives in the 3-position as well as 7-aminocephalosporanic acid or its derivatives in the 3-position. Additionally, the adduct may be treated with an appropriate acid to obtain free N-acyl-cephalosporin C or its deacetoxy derivative which is then converted into the corresponding salt such as an alkali metal salt or a trialkyl amine salt.

The 3-position derivatives of N-acyl-cephalosporin C can be obtained by reacting N-acyl-cephalosporin C or an adduct or salt thereof with an alkali metal azide or a thiol of the general formula (IV): $HS-R_3$ wherein $R_3$ is as defined above, or a salt thereof.

The reaction may be conducted in an aqueous solvent, adjusting to pH 5.0–8.0. The aqueous solvent to be used includes water itself or a mixture of water and an organic solvent such as a lower aliphatic alcohol (e.g., methanol), acetone, dioxane or the like. It is preferred to select a suitable solvent, taking into consideration its solubility in water. It is convenient to add to the reaction mixture, for example, a phosphate buffer in order to control the pH value during the reaction. It also is generally desired to heat the reaction mixture.

Preferred examples of the thiol of the formula (IV) include thiadiazole-thiols such as 1,3,4-thiadiazole-2-thiol or 5-methyl-1,3,4-thiadiazole-2-thiol; tetrazole-thiol such as tetrazole-5-thiol or 1-methyltetrazole-5-thiol; oxadiazole-thiol such as 1,3,4-oxadiazole-2-thiol or 5-methyl-1,3,4-oxadiazole-2-thiol, and like compounds.

The resulting 3-substituted compound may be isolated by acidifying the aqueous reaction mixture and extracting same with an organic solvent such as ethyl acetate. When desired, a purification step such as the use of charcoal may be conducted during the above procedure. Furthermore, the organic extract may be used as such for the next reaction in order to remove the acyl group at the 7-position. However, when water or proton-active organic solvents are present in the mixture, they should be removed before the next reaction as explained below.

The thus obtained cephalosporin derivatives of the formula (I) or adducts or salts thereof may be further treated to remove their acyl group at the 7-position to give 7-aminocephalosporanic acid and its 3-substituted derivatives.

That is, 7-aminocephalosporanic acid or its 3-substituted derivatives may be obtained by converting the cephalosporin derivative of the formula (I) or adduct or salt thereof into a protected derivative by reacting the carboxy groups in the 4-and 5-positions to form an easily hydrolyzable ester or mixed anhydride, reacting the resultant protected product with an iminohalide forming agent and then with an imino-ether forming agent to give the corresponding imino-ether compound and then hydrolyzing the latter.

As reagents to be used for protection of the carboxy groups of the cephalosporin derivative (I) there may be mentioned phosphine-halogen compounds of the general formula (V):

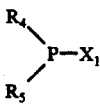

wherein $X_1$ is a halogen atom, $R_4$ is a lower alkyl or alkoxy group or a halogen atom and $R_5$ is a halogen atom or a lower alkoxy group, but when both of $R_4$ and $R_5$ are lower alkoxy groups, they may form a ring together with P atom, or a silicone-halogen compound of the general formula (VI):

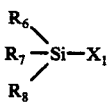

, wherein $X_1$ is a halogen atom, $R_6$ is a lower alkyl or alkoxy group or a halogen atom and $R_7$ and $R_8$ are a lower alkyl or alkoxy group.

Preferred examples of these phosphine or silicone-halogen compounds include

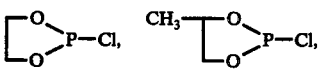

$CH_3OPCl_2$, $C_2H_5OPCl_2$, $C_4H_9OPCl_2$, $CH_3PCl_2$, $C_4H_9PCl_2$, $PCl_3$, $ClCH_2CH_2OPCl_2$, $(CH_3)_3SiCl$, $CH_3(CH_3O)_2SiCl$, $(CH_3O)_3SiCl$, $CH_3O(CH_3)_2SiCl$, $(CH_3)_2SiCl_2$, $(CH_3O)_2SiCl_2$, $CH_3(CH_3O)SiCl_2$.

Even more preferred examples include

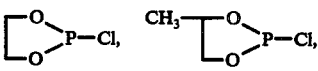

$(CH_3)_3SiCl$, $CH_3(CH_3O)_2SiCl$, $CH_3O(CH_3)_2SiCl$, $(CH_3O)_3SiCl$. In addition $COCl_2$, $CH_3COCl$ and like compounds which are carbon-halogen compounds may also be used. In brief, the protection of the carboxy groups is effected in order to make the carboxy groups inert in the subsequent imino-halide formation and imino-ether formation and therefore the nature of the protecting group is not of any particular importance. It is, however, desired to select a suitable reagent among the above-mentioned examples, taking into consideration the ease of hydrolysis, the cost of reagents, and the ease of treatment.

The reaction for converting the carboxy groups into its protected form may be conducted under anhydrous condition in an inert organic solvent such as methylene chloride, ethylene chloride, tetrahydrofuran or chloroform and in addition, in the presence of an organic base such as triethylamine, N-methylmorpholine, N-methylpiperidine, quinoline, pyridine, dimethylaniline or analogues thereof.

The reaction product is then reacted with an imino-halide forming agent such as phosphorus pentachloride, phosphorus oxychloride or phosgene to convert the amide bond in the 7- and 5'- positions of the cephalosporin derived from the compound of the formula (I), into the corresponding imino-halide. To the reaction mixture is then added a lower alcohol such as methanol, propanol, butanol, amyl alcohol, ethylene glycol, propylene glycol, ethylenechlorohydrin, alkoxyethanol or the like, to convert the imino halide into the corresponding imino-ether.

Moreover, the reaction mixture may be subjected to the protection of the carboxy groups as is, and then used in the above two reactions.

The resulting imino-ether compound is subjected to hydrolysis with water to convert it into the desired 7-aminocephalosporanic acid and its 3-substituted derivatives.

The hydrolysis may be conducted under acidic conditions, preferably at a pH below 3. Furthermore, when N-acyldeacetoxy cephalosporin C is used, hydrolysis may ever be conducted at pH 1.

The reaction mixture, after the hydrolysis, is adjusted to the isoelectric point of the resultant 7-amino compound, as a result of which the desired compound may be obtained as a precipitate. The thus obtained precipitate is separated and dried in accordance with conventional methods.

The desired compounds according to the method of the invention are obtained in very high yield and purity.

The following examples are given to aid in understanding the invention, and variations may be made by one skilled in the art without departing from the spirit and scope of the invention.

EXAMPLE 1

To 20 ml of "an elution from resin" containing 30 mg/ml of cephalosporin C were added about 0.2 g of sodium borate, which was adjusted to pH 9.0 with a dilute sodium hydroxide solution. To this solution were added 5 ml of a solution of the mixed anhydride in ethyl acetate (contains 2.5 moles per mole of cephalosporin C) which was prepared from pivaloyl chloride and the N-methylmorpholine salt of methylthioacetic acid and stirred vigorously at 0°–10° C for about an hour adjusting to pH 9 with dilute sodium hydroxide. After monitoring the completion of the reaction by thin-layer chromatography (benzene:acetic acid:pyridine:water = 15:3:10:12, sprayed by a solution of iodo azide as a coloring agent and heated), the reaction mixture was adjusted to pH 5–6 with dilute sulfuric acid.

The organic layer was removed and the aqueous layer was diluted with water to 30 ml (a solution corresponding to 2% cephalosporin C solution). To 15 ml of the aqueous solution was added 0.43 ml of quinoline (5 moles per mole of cephalosporin C) and adjusted to pH 3.0 with dilute sulfuric acid, while stirring. Crystals soon appeared. After stirring for an hour, the precipitated crystals were collected, washed with a small amount of ice-water and then with ethyl acetate and dried overnight in a vacuum desiccator. Thus, the quinoline adduct of N-methylthioacetyl-cephalosporin C was obtained. Yield: 450 mg (97% purity by UV assay), 98%.

IR 1790 cm$^{-1}$ ($\beta$-lactam), UV $\lambda$ max 264 m$\mu$.

EXAMPLE 2

Three portions each of 15 ml of the reaction mixture (2% solution calculated as cephalosporin C) obtained from 3% cephalosporin C solution in accordance with Example 1 were diluted as follows and to each was added 0.43 ml of quinoline (5 moles per mole of cephalosporin C), followed by the treatment according to Example 1.

Yields of quinoline adduct of N-methylthioacetyl-cephalosporin C were as follows. (Figures in parenthesis show yields when diluted with 5% sodium chloride solution)

| | | Yield |
|---|---|---|
| a) | 1 % solution, 30 ml | 426mg, 93% (441mg), (96%) |
| b) | 0.5 % solution, 60 ml | 415mg, 90% (436mg), (94%) |
| c) | 0.3 % solution, 100 ml | 380mg, 83% (403mg), (87%) |

EXAMPLE 3

To 20 ml of "an elution from resin" containing 15 mg/ml (by UV assay) of cephalosporin C was added about 0.2 g of sodium hydrogen phosphate and adjusted to pH 9.0 with a dilute sodium hydroxide solution. To this mixture were added 5 ml of a solution of the mixed anhydride* in ethyl acetate prepared from potassium methylthioacetate, propionyl chloride and a slight amount of N-methylmorpholine and stirred vigorously at 0°–10° C for about an hour, while maintaining the pH at 9 with a dilute sodium hydroxide solution. The reaction mixture was adjusted to pH 5–6. After separating out the organic layer, the aqueous layer was diluted with a 5% sodium chloride solution to make 30 ml (corresponds to 1% solution calculated as cephalosporin C). (*contains 2.5 moles per mole of cephalosporin C)

To 15 ml of the solution was added 0.22 ml of isoquinoline (5 moles per mole of cephalosporin C) and adjusted to pH 3.0 with dilute sulfuric acid at 10° C with stirring. Very soon crystals separated out. After stirring for 1 hour, the crystals were collected and washed with a small amount of ice-water, then with ethyl acetate and dried overnight in a vacuum desiccator, by which 228 mg (Yield: 97%) of the isoquinoline adduct of N-methylthioacetylcephalosporin C, purity of 97% (by UV assay) were obtained. UV λ max 263 mμ.

15 ml of the remaining reaction solution were diluted with a 5% sodium chloride solution to 30 ml (corresponds to 0.5% solution calculated as cephalosporin C). After adding 0.22 ml of quinoline to the solution, the mixture was adjusted to pH 3.0 and stirred at 5°–10° C. Very soon crystals separated out. The crystals were collected after an hour, washed with ice-water and with ethyl acetate and dried in vacuo. 226 mg of isoquinoline adduct of N-methylthioacetyl-cephalosporin C having 97% purity were obtained.

EXAMPLE 4

To 10 ml of "an elution from resin" which was adjusted so as to contain 10 mg/ml of cephalosporin C, was added about 0.04 g of sodium borate and adjusted to pH 9.0 with a dilute sodium hydroxide solution. To this mixture were added 3 ml of a solution of the mixed anhydride (contains 2.5 moles per mole of cephalosporin C) in ethyl acetate prepared from potassium methylthioacetate, a slight amount of N-methylmorpholine and acetyl chloride. The mixture was vigorously stirred at 10°–20° C for about an hour, maintaining the pH at 9.0 with a dilute sodium hydroxide solution.

To the reaction mixture were added 0.1 ml of quinoline and then 10% phosphoric acid solution to adjust some to pH 3.0 with stirring. Very soon crystals separated out. After stirring for about 1 hour, the crystals were collected and washed with a small amount of ice-water, then with ethyl acetate and dried overnight in a vacuum desiccator, by which 145 mg of the quinoline adduct of N-methylthioacetyl-cephalosporin C (98% purity) were obtained.

IR and UV spectrum of the product coincided with those of an authentic sample of the compound.

When N-acetylation was carried out with the use of acetic anhydride instead of the above-mentioned mixed acid anhydride, the desired crystals of the quinoline adduct could not be obtained.

EXAMPLE 5

The quinoline adduct of N-methylthioacetyl-cephalosporin C, 150 mg (98% purity) was obtained by the procedure in accordance with Example 4, but an ethyl acetate solution of the acid anhydride prepared from methylthioacetyl chloride and N-methylmorpholine salt of methylthioacetic acid was used instead of the solution of the mixed anhydride of methylthioacetic acid and acetic acid.

EXAMPLE 6

The quinoline adduct of N-ethylthioacetyl-cephalosporin C, 125 mg (96% purity) was obtained by the procedure in accordance with Example 4, but an ethylthioacetate solution of the mixed anhydride prepared from potassium ethylthioacetate, propionyl chloride and a slight amount of N-methylmorpholine was used instead of the mixed anhydride of methylthioacetic acid and acetic acid in Example 4.

IR 1790 cm$^{-1}$, UV λ max 263 mμ.

EXAMPLE 7

Instead of the mixed anhydride of methylthioacetic acid as and acetic acid in Example 4, ethyl acetate solutions of (a) the mixed anhydride prepared from potassium isopropylthioacetate, pivaloyl chloride and a slight amount of N-methylmorpholine, (b) the mixed anhydride from potassium isobutylthioacetate, pivaloyl chloride and a slight amount of N-methylmorpholine, (c) the mixed anhydride from potassium α-methylthiopropionate, propionyl chloride and a slight amount of N-methylmorpholine and (d) the mixed anhydride from potassium methylsulfinylacetate, pivaloyl chloride and a slight amount of N-methylmorpholine were treated in accordance with the procedure Example 4, the results of which were as follows:
  (a) Quinoline adduct of N-isopropylthioacetyl-cephalosporin C, 108 mg (95% purity), UV λ max 263 mμ.
  (b) Quinoline adduct of N-isobutylthioacetyl-cephalosporin C, 105 mg (96% purity), UV λ max 263 mμ.
  (c) Quinoline adduct of N-α-methylthiopropionyl-cephalosporin C, 134 mg (97% purity), UV λ max 263 mμ.
  (d) Quinoline adduct of N-methylsulfinylacetyl-cephalosporin C, 138 mg (94% purity), UV λ max 263 mμ.

EXAMPLE 8

Instead of the mixed anhydride of methylthioacetic acid and acetic acid as in Example 4, ethyl acetate solutions of (a) the mixed anhydride prepared from potassium β-methylthiopropionate, pivaloyl chloride and a slight amount of N-methylmorpholine, and (b) the mixed anhydride from potassium β-ethylthiopropionate, pivaloyl chloride and a slight amount of N-methylmorpholine were used and treated in accordance with the procedure of Example 4, the results of which are as follows:

(a) Quinoline adduct of N-β-methylthiopropionyl-cephalosporin C, 100 mg (96% purity), IR 1790 cm$^{-1}$, UV λ max 263 mμ.

(b) Quinoline adduct of N-β-ethylthiopropionyl-cephalosporin C, 82 mg (96% purity), IR 1790 cm$^{-1}$, UV λ max 263 mμ.

EXAMPLE 9

0.63 g of dry quinoline adduct of N-methylthioacetyl-cephalosporin C, 0.3 g of triethylamine and 0.4 g of dimethylaniline were added to 10 ml of anhydrous methylene chloride and to the mixture was added dropwise a solution of 0.43 g of trimethylsilyl chloride in methylene chloride at 0° C with stirring. After about 30 minutes, 0.5 g of fine powdered phosphorus pentachloride were added to the resulting clear solution cooled at −30° C and stirred for 2 hours at −20°−−5° C. Then the mixture was again cooled to −30° C. and 3 ml of anhydrous isobutanol were added dropwise to the cooled mixture, stirred for 2 hours at −30°−−10° C and kept overnight at −20° C. 3 ml of ice-water were then added to this mixture and stirred for 30 minutes, maintaining the pH at 2.0–2.5 with ammonium carbonate. Then the mixture was gradually adjusted to pH 3.5 (the isoelectric point) and kept overnight in an ice-box. The precipitated crystals were collected by centrifugation, washed with a small amount of cooled 60% acetone-water and then with acetone and dried.

7-Aminocephalosporanic acid, 0.23 g (Yield: 84%, Purity: 98% by UV assay) was obtained.

IR 1800 cm$^{-1}$, UV λ max 262 mμ.

EXAMPLE 10

Instead of trimethylsilyl chloride as in Example 9, (a) 2-chloro-1,3,2-dioxaphospholane 0.5 g, (b) 2-chloro-4-methyl-1,3,2-dioxaphospholane 0.55 g, (c) trimethoxysilyl chloride 0.63 g and (d) dimethyl-methoxysilyl chloride 0.5 g respectively were used and treated in a manner similar to that of Example 9. 7-Aminocephalosporanic acid was obtained in the respective yields of (a) 0.22 g, (b) 0.24 g, (c) 0.23 g and (d) 0.23 g.

EXAMPLE 11

Instead of isobutyl alcohol as in Example 9, (a) anhydrous methanol and (b) n-butanol respectively were used and treated in a manner similar to that of Example 9. 7-Aminocephalosporic acid was obtained in the respective yields of (a) 0.25 g and (b) 0.21 g.

EXAMPLE 12

To 20 ml of "an elution from resin" adjusted to contain 10mg/ml of cephalosporin C was added about 0.08 g of sodium borate and adjusted to pH 9.0 with dilute sodium hydroxide solution. To this solution were added 5 ml of a solution of the mixed anhydride in ethyl acetate (contains 4 moles per mole of cephalosporin C) which was prepared from potassium methylthioacetate, a slight amount of N-methylmorpholine and ethyl chlorocarbonate and stirred vigorously at 0°–5° C. The mixture was allowed to react for about 1 hour, maintaining the pH at 9 with a dilute sodium hydroxide solution. To the reaction mixture was added 0.2 ml of quinoline and the resultant mixture was adjusted to pH 3.0 with stirring. The mixture was then saturated with sodium chloride, stirred for about 1 hour, filtered to collect the resulting crystals, which were washed with ice-water and ethyl acetate and then dried. Thus, the quinoline adduct of N-methylthioacetyl-cephalosporin C, 260 mg (97% purity) was obtained.

EXAMPLE 13

(a) 3.8 g of the quinoline adduct of 5′-N-methylthioacetyl-cephalosporin C, were suspended in 25 ml of water, adjusted to pH 6.5 with 2N-aqueous sodium hydroxide solution and washed several times with methylene chloride. Then to the mixture were added 0.8 g of 1-methyltetrazole-5-thiol and 0.5 g of sodium hydrogen phosphate and adjusted again to pH 6.5 with sodium hydroxide. The mixture was stirred for 5-8 hours at 60°-70° C. (The reaction mixture was monitored by thin-layer chromatography.) After completing the reaction, the mixture was adjusted to pH 2.0 with dilute sulfuric acid, extracted several times with ethyl acetate, washed four times with a small amount of an aqueous saturated sodium chloride solution, dried over magnesium sulfate and then distilled in vacuo to remove the solvent. The residue was treated with n-hexane to solidify it, by which 2.3 g of 7-[5′-N-methylthioacetamido)-adipoamido]-3-(1″-methyltetrazol-5″-yl)-thiomethyl-3-cephem-4-carboxylic acid (Yield: 84%) were obtained.

IR (KBr) 1770 cm$^{-1}$, UV λ max 272 mμ.

(b) 1.1 g of the compound obtained in (a) above were dried over phosphorus pentoxide at 70°–80° C in vacuo. Dry methylene chloride (10 ml), dimethylaniline (2.4 g) and methyldichlorophosphite (1.3 g) were added to the above dried compound and stirred at room temperature. After 30 minutes, the clear solution was cooled to −30° C. To this mixture were added, the stirring, 1.2 g of phosphorus pentachloride which was allowed to react for 2 hours at −20°-° C and then cooled to −40° C again. 2.6 g of anhydrous methanol were added dropwise to the reaction mixture, stirred for 2 hours at −20° C−−5° C and left to stand overnight at −20° C. The mixture was put into 7 ml of ice-water, stirred for 20 minutes, and then gradually adjusted to pH 3.5 with ammonium carbonate. Then the mixture was kept overnight, and adjusted to pH 3.5 again and the crystals were collected by centrifugation. The crystals were washed with cold 60% aqueous acetone, centrifuged and again washed with acetone. 0.55 g (Yield: 86%) of 7-amino-3-(1′-methyltetrazol-5′-yl)-thiomethyl-3-cephem-4-carboxylic acid were obtained.

IR: 1800 cm$^{-1}$, UV λ max: 272 mμ.

(c) The experiment was repeated with the same reagents and treatment as above but 3.1 g of trimethoxysilylchloride were used instead of methyldichlorophosphite. The yield was 80%.

(d) The experiment was repeated with the same reagents and treatment as above, but 1.6 g of acetyl chloride and 3.7 g of ethylene glycol were used instead of methyldichlorophosphite and methanol respectively. The yield was 73%.

EXAMPLE 14

(a) 5-Methyl-1,3,4-thiadiazole-2-thiol instead of 1-methyltetrazole-5-thiol was used and treated in the same way as in (a) of Example 13, by which 2.4 g (Yield: 84%) of 7-[(5′-methylthioacetamido)-adipoamido]-3-(5″-methyl-1″,3″,4″-thiaziazol-2″-yl)-thiomethyl-3-cephem-4-carboxylic acid were obtained.

IR: 1780 cm$^{-1}$, UV λ max: 272 mμ.

(b) 1.2 g of the product obtained in (a) above were treated in the same way as in (b) of Example 13, by which 0.6 g (Yield: 87%) of 7-amino-3-(5′-methyl- 1',3',4'-thiadiazol-2'-yl)-thiomethyl-3-cephem-4-carboxylic acid were obtained.

IR: 1800 cm$^{-1}$, UV λ max: 272 mμ.

EXAMPLE 15

(a) 1,3,4-Thiadiazole-2-thiol instead of 1-methyltetrazole-5-thiol in (a) of Example 13 was used and treated in the same way as in (a) of Example 13, by which 2.3 g (Yield: 82%) of 7-[(5'-N-methylthioacetamido)-adipoamido]-3-(1',3',4'-thiaziazol-2'-yl)-thiomethyl-3-cephem-4-carboxylic acid were obtained.

IR: 1780 cm$^{-1}$, UV λ max: 270 mμ.

(b) 1.1 g of the product obtained in (a) above were used and treated in the same way as in b) of Example 13, by which 0.5 g (Yield: 83%) of 7-amino-3-(1',3',4'-thiadiazol-2'-yl)-thiomethyl-3-cephem-4-carboxylic acid were obtained.

IR: 1800 cm$^{-1}$, UV λ max: 270 mμ.

What we claim is:

1. A compound of the formula:

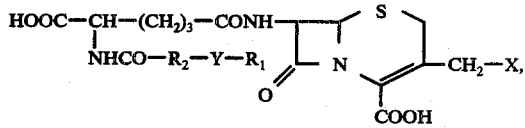

wherein $R_1$ is a lower alkyl, phenyl or benzyl group, $R_2$ is a lower alkylene group, Y is a sulfur atom or a sulfinyl group and X is a hydrogen atom, an acetoxy group, or an azido group, and adducts thereof with quinoline or isoquinoline.

2. N-Methylthio-acetyl-cephalosporin C or quinoline or isoquinoline adduct thereof in accordance with Claim 1.

3. N-Ethylthio-acetyl-cephalosporin C or quinoline adduct thereof in accordance with claim 1.

4. N-Isopropylthio-acetyl-cephalosporin C or quinoline adduct thereof in accordance with claim 1.

5. N-Isobutylthio-acetyl-cephalosporin C or quinoline adduct thereof in accordance with claim 1.

6. N-α-Methylthio-propionyl-cephalosporin C or quinoline adduct thereof in accordance with claim 1.

7. N-methylsulfinylacetyl-cephalosporin C or quinoline adduct thereof in accordance with claim 1.

8. N-α-Methylthio-propionyl-cephalosporin C or quinoline adduct thereof in accordance with claim 1.

9. N-β-Ethylthio-propionyl-cephalosporin C or quinoline adduct thereof in accordance with claim 1.

* * * * *

UNITED STATES PATENT OFFICE
CERTIFICATE OF CORRECTION

Patent No. 4,091,217          Dated May 23, 1978

Inventor(s) Toshiyasu Ishimaru et al

It is certified that error appears in the above-identified patent and that said Letters Patent are hereby corrected as shown below:

Column 1, lines 35-36: "position thereof in the 3-which" should read -- thereof in the 3-position which --.

Column 2, line 18: "is" should read -- or --; lines 33-34: "recovering an adducts" should read -- recovering adducts --; line 38: "both" should read -- from both --.

Column 6, line 14: "may ever" should read -- may even --.

Column 7, line 64: "some" should read -- same --.

Column 8, line 34: "acid as and acetic acid" should read -- acid and acetic acid as --.

Column 10, line 22: "7-[5'-N-methylthioacetamido)-" should read -- 7-[(5'-N-methylthioacetamido)- --; line 32: "added, the" should read -- added, with --; line 34: "-20°-°C" should read -- -20°-0°C --.

UNITED STATES PATENT OFFICE
CERTIFICATE OF CORRECTION

Patent No. 4,091,217    Dated May 23, 1978

Inventor(s) Toshiyasu Ishimaru et al

It is certified that error appears in the above-identified patent and that said Letters Patent are hereby corrected as shown below:

Column 11, line 5: "$cm^{31\ 1}$," should read -- $cm^{-1}$, --.

Column 12, line 26: "N-$\alpha$-Methylthio-" should read -- N-$\beta$-Methylthio- --.

Signed and Sealed this

Twenty-ninth Day of May 1979

[SEAL]

Attest:

RUTH C. MASON
Attesting Officer

DONALD W. BANNER
Commissioner of Patents and Trademarks